United States Patent
Scalesciani

(10) Patent No.: US 9,474,718 B2
(45) Date of Patent: Oct. 25, 2016

(54) COLLAGEN POWDER, COMPOSITION AND USE

(71) Applicant: EURORESEARCH S.r.l., Milan (IT)

(72) Inventor: Juan Francisco Scalesciani, Buenos Aires (AR)

(73) Assignee: EUROPESEARCH S.R.L., Milan (IT)

( * ) Notice: Subject to any disclaimer, the term of this patent is extended or adjusted under 35 U.S.C. 154(b) by 0 days.

(21) Appl. No.: 14/890,521

(22) PCT Filed: May 15, 2013

(86) PCT No.: PCT/EP2013/001432
§ 371 (c)(1),
(2) Date: Nov. 11, 2015

(87) PCT Pub. No.: WO2014/183770
PCT Pub. Date: Nov. 20, 2014

(65) Prior Publication Data
US 2016/0106674 A1    Apr. 21, 2016

(51) Int. Cl.
| | | |
|---|---|---|
| A61K 9/50 | (2006.01) |
| A61K 9/14 | (2006.01) |
| A61K 35/24 | (2015.01) |
| A61K 33/38 | (2006.01) |
| A61K 33/32 | (2006.01) |
| A61L 9/00 | (2006.01) |
| A61K 38/39 | (2006.01) |
| A61K 31/315 | (2006.01) |
| A61K 31/28 | (2006.01) |
| C08H 1/06 | (2006.01) |
| C08L 89/06 | (2006.01) |
| A61L 26/00 | (2006.01) |
| A61K 9/00 | (2006.01) |
| A61K 33/30 | (2006.01) |
| A61K 35/644 | (2015.01) |
| A61K 45/06 | (2006.01) |
| A61K 47/36 | (2006.01) |

(52) U.S. Cl.
CPC ............... *A61K 9/14* (2013.01); *A61K 9/0014* (2013.01); *A61K 9/146* (2013.01); *A61K 33/30* (2013.01); *A61K 33/38* (2013.01); *A61K 35/644* (2013.01); *A61K 38/39* (2013.01); *A61K 45/06* (2013.01); *A61K 47/36* (2013.01); *A61L 26/0033* (2013.01); *C08H 1/06* (2013.01); *C08L 89/06* (2013.01)

(58) Field of Classification Search
None
See application file for complete search history.

(56) References Cited

U.S. PATENT DOCUMENTS

| 5,153,067 A * | 10/1992 | Yoshida | C08L 89/06 428/402 |
| 5,196,185 A | 3/1993 | Silver et al. | |
| 7,923,031 B2 * | 4/2011 | Moller | A61J 1/067 424/489 |
| 9,131,713 B2 * | 9/2015 | Dick | A23C 9/137 |

FOREIGN PATENT DOCUMENTS

| EP | 0421450 A2 | 4/1991 | |
| EP | 0 507 193 A1 * | 10/1992 | A61K 7/48 |

OTHER PUBLICATIONS

Moreno-Alvarez et al.; Lung (2010) 188:97-105.*
International Search Report based on International Application No. PCT/EP2013/001432. (2 pages)( Jul. 11, 2013).

* cited by examiner

*Primary Examiner* — Jeffrey T Palenik
(74) *Attorney, Agent, or Firm* — Lucas & Mercanti, LLP

(57) ABSTRACT

Collagen powder in which at least 99.5% of the particles have a maximum size of 80 microns 25% to 45% by volume of the particles have a size of more than 30 microns and 35% to 50% by volume of the particles have a size in the range of 20 to 70 microns.

16 Claims, 1 Drawing Sheet

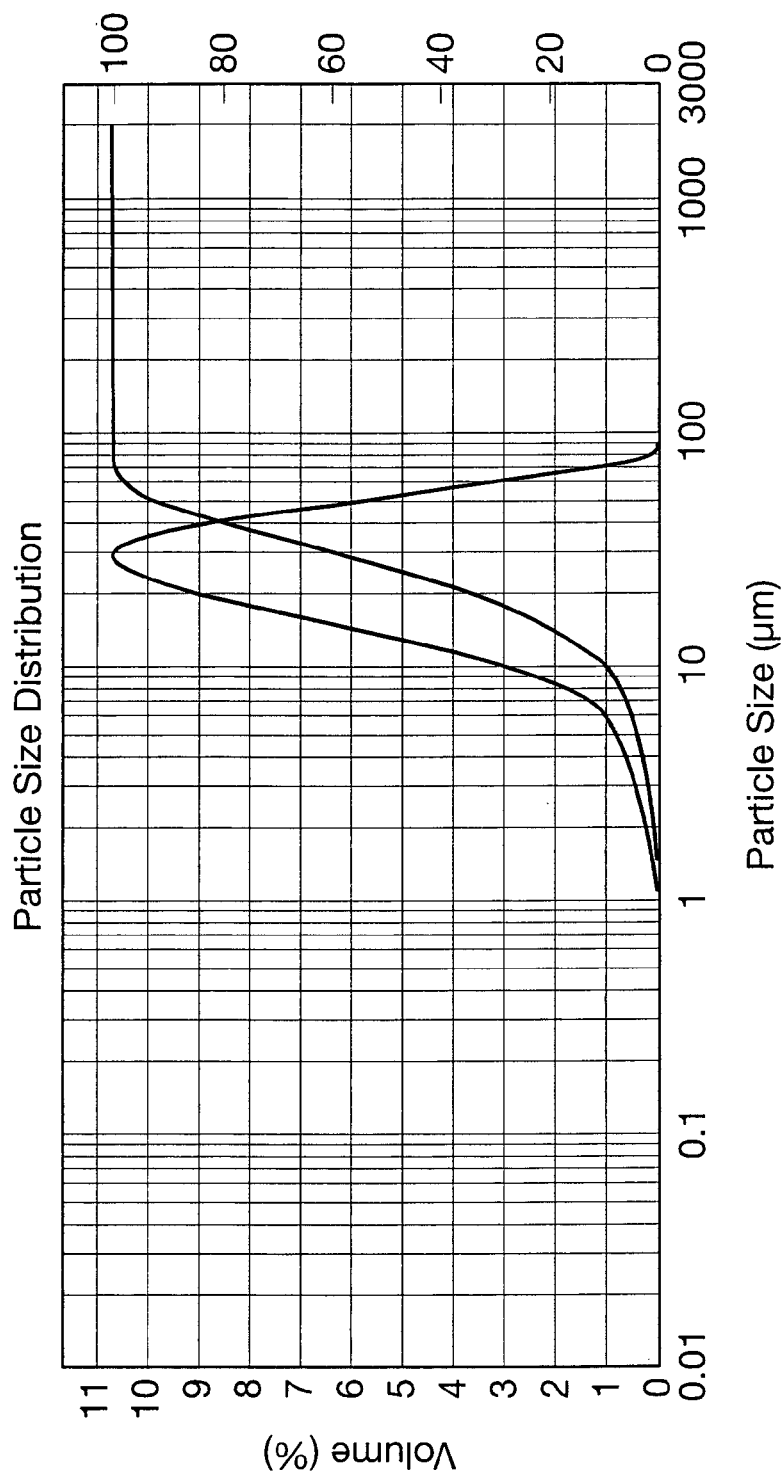

COLLAGEN POWDER, COMPOSITION AND USE

CROSS-REFERENCE TO RELATED APPLICATION

This application is a 371 of PCT/EP2013/001432, filed May 15, 2013.

The present invention relates to a collagen powder having a specific particle size, to a pharmaceutical, medical or cosmetic composition containing said collagen powder and to its use. A preferred use of the collagen of the invention is in the form of a spray composition, particularly for the treatment of wounds.

BACKGROUND OF THE INVENTION

Collagen, a scleroprotein having a molecular weight of about 297.000 Daltons, is the most abundant fibrous protein in the higher vertebrates because it is the principal constituent of the skin, the connective tissue and the organic material present in the bones and the teeth. This protein represents approximately one third of the total amount of proteins in the human body.

Various types of collagen occur naturally and they are all composed of three polypeptides chains which have a constant periodicity and are arranged in a triple helix: the difference between the various types of collagen is due to small differences in the primary structure of the chains, i.e. in the aminoacidic sequence of the chain itself.

Type I collagen, which is the basic constituent of the skin, the bones and the tendons, may be regarded as the most abundant of the various types of collagen; the triple helix has two $\alpha1(I)$ and one $\alpha2(I)$ chain composition where the $\alpha1(I)$ and the $\alpha2(I)$ chains are homologous.

Between the two $\alpha1$ chains and the $\alpha2$ chain there are electrostatic interactions, hydrogen bonds and sulfur bond bridges which together with the presence of hydroxyproline confer to the molecule the typical characteristic of spatial rigidity.

The production of collagen in the bodies of mammals is preceded in the cell by the formation of a larger biosynthetic precursor, called procollagen assembled in the triple helix but containing the two non helicized terminal parts; the procollagen is then degraded by specific enzymes which cut off these parts and form collagen.

Out of the cell the molecule assembles itself in polymeric forms called fibrils and fibers: in the tendon this assembling is spatial, while in the skin is planar; fibrils and fibers are the real structure of collagen in the mammals.

The role of collagen in wound healing is well known: platelet aggregation takes place when platelets come in contact with a suspension of collagen fibers (Collagen in health and disease by Barnes M. J., Weiss J. B. and Jayson M.; VI Ed., Churchill Livingstone Ed., Longman Group Ltd., 1982, chapter 10, page. 179) and the protein is fundamentally involved in the mechanism of cicatrization.

The literature discloses the use of collagen as a stimulating agent in the process of wound healing by interaction with various growth factors, for its action of capturing fibronectin, as well as the migration and replication of cells which are the consequence thereof.

Collagen is currently used as a wound-healing agent in clinical surgery, in the treatment of burns, as a vehicle in surgical prosthesis (suture threads, gauzes, etc.) as a material for implantation, or as a component in compositions in the pharmaceutical and cosmetic sector. A known type of compositions containing collagen are spray compositions; a spray is easy to apply to a wound or to skin without contacting them with hands or an applying device. On the other side, it is not very easy to obtain a spray composition that ensures a uniform distribution of the collagen particles on the target surface.

Many studies have demonstrated that collagen having small particle sizes has a number of advantages as a material for skin dressing, and in particular wound dressing, e.g. the fact that small particles have large surface area and that it is easier to prepare spray compositions. Commercially available powder collagens are now mainly in the form of a powder having small particle size in order to improve its adhesion to moist surfaces and to improve its use in the form of a spray.

Small size particles are also seen as a critical feature for collagen in view of the stability of the collagen polymer structure. In fact it was shown that polymer degradation can also be affected by the particle size. For instance, the rate of biomatrix polymer degradation was found to increase with increasing particle size in vitro. It was thought that in smaller particles, degradation products of biomatrix formed can diffuse out of the particles easily while in large particles, degradation products are more likely "trapped" within the polymer matrix for a longer period so as to cause autocatalytic degradation of the polymer material. Therefore, it was hypothesized that larger particles will contribute to faster polymer degradation as well as to a faster decrease of the bioactivity of the product. Clinical aspects will be more influenced from collagen biomatrix preservation; in fact, more stability of the product will be reflected in faster tissue re-epithelialization.

For all the above reasons powdered collagen products that are commercially available preferably have a considerably small particle size.

U.S. Pat. No. 196,185 discloses particulate collagen formed from type I collagen, type III collagen and mixtures thereof, having a particle size from 1 to 50 microns and in particular from 5 to 25 microns. The document further discloses compositions containing such powdered collagen which may be applied as wound dressing. The collagen microparticles of said composition are sufficiently small to be airlessly sprayed through an orifice to form a dry film on the surface of skin or wounds, which promotes wound healing and tissue growth.

WO0160922, in the name of the present applicant, discloses a process for the production of micronized collagen having a particle size of from 5 to 30 microns, generally not more than 20 microns and preferably of approximately 18 microns. This process enables the production of powered collagen which is non-denatured, anallergic, free from impurities or contaminants and in a finely micronized form. The product obtained by this method exhibits good adhesion of the collagen to the wound and, due to its particle size, it may be used in a spray composition.

Thus, according to the prior art, the wound healing properties of powdered collagen are improved by reducing the maximum size of the particles. The preferred particle size according to the prior art is below 20-25 microns.

SUMMARY OF THE INVENTION

An aim of the present invention is to provide a powdered collagen product that exhibits an improved wound healing effect compared to the products disclosed in the prior art. Another aim of the present invention is to provide compositions, in particular spray compositions, for wound healing comprising such a powdered collagen product.

The above aims are reached by means of the present invention.

In fact, it has now been found that, contrary to the commonly accepted rule, it is not necessary that the vast majority of collagen particles have a size of less than 20 or 25 microns, in particular when the powder is to be used in a spray composition. Additionally, it was found that the distribution of the size of the collagen particles in a given powdered collagen product also plays an important role in the wound healing effect exhibited by such a product.

Namely, in addition to the new, higher, maximum size of the particles in a collagen powder, the distribution of the particle sizes below said maximum plays an important role in its wound healing properties. Furthermore, it was surprisingly found that a product comprising, in addition to the particles having a size of less than 25 microns, a certain amount of larger particles, up to 80 μm (microns), exhibits superior wound healing properties with respect to known collagen powders.

Thus, the present invention provides a product that comprises a significant portion of particles having a size of greater than 30 microns, which improves its wound healing properties. At the same time the composition maintains excellent behaviour in sprays, providing a uniform distribution of the collagen particles, and is stable in time, i.e. no clumps or aggregates are formed in the composition.

It is an object of the present invention a collagen powder according to claim 1. A further object of the invention is the use of said powder in wound healing and its use for the preparation of a wound healing composition.

The product of the present invention may be incorporated in a variety of wound healing compositions, including spray compositions according to claim 15. Preferably, the composition comprises a carrier; an exemplary carrier is rice starch. According to a preferred embodiment of the invention, the particle size distribution of the rice starch or other carrier for the collagen follows the distribution of the particle size of the collagen; in other words, the granulometry data of the carrier fall within the ranges (above discussed) of the sizes of the collagen powder.

The invention will now be further disclosed with reference to the enclosed exemplary and not-limiting drawings, where:

FIG. 1 shows the particle size distribution of a collagen product according to the present invention and the relationship between the dimension of the particles and the percentage in volume of the particles having a chosen dimension with regards to the total amount of particles.

DETAILED DESCRIPTION OF THE INVENTION

The present invention provides collagen powder wherein at least 99.5% of the particles have a maximum size of 80 microns and at least 25% by volume of the particles have a size of more than 30 microns. Preferably, the amount of particles having a size of more than 30 microns is in the range of 25% to 45% by volume.

According to an exemplary embodiment of the invention, at least 15% by volume of the particles have a size of more than 40 microns; more preferably, the amount of particles having a size of more than 40 microns is in the range of 15% to 22% by volume. Preferably, the amount of particles having a size of more than 50 microns is in the range of 8 to 13% by volume.

Preferably, the collagen powder of the present invention contains no more than 10% by volume of particles having a size of 10 microns or less and the amount of particles having a size within 10 to 20 microns is in the range of 25% to 35%, most preferably about 30% by volume.

A preferred collagen according to the invention is a combination of the above mentioned preferred distribution ranges, wherein 35% to 50% by volume of the particles have a size in the range of 20 to 70 microns.

A particle size distribution of a powder according to the present invention is shown in FIG. 1.

Collagen suitable for the present invention is Type I collagen, preferably obtained from horse and/or cows (i.e. bovine) tendons, preferably horse tendons. Collagen is normally obtained from said animal organs in the required stable and non-denatured form by extraction and purification processes such as, for example, those described in JP 2886164. The product thus obtained is normally a viscous solution which contains from 0.1 to 2.0% of collagen and which, in order to be used in therapeutic applications, is normally subjected to further conversions; it is, for example, converted by lyophilisation into a pad having a water content of approximately 17%, or by drying, into a lamellar structure having a water content of approximately 20%. The product of the present invention may be obtained by screening a collagen powder produced according to any process known from the prior art. The powered product may be obtained from any type of collagen, but it is preferred to use type I native collagen. Preferably, the powered product has the spatial assembly of the fibrils and fibers, as the collagen obtained from tendons, e.g. preferably from horse tendons, retains its native structure.

In an exemplary embodiment, the collagen powder may be produced according to a process which utilizes commercially available atomizers. According to said process an aqueous viscous solution of collagen with a concentration of 0.1 2.0%, having a pH of from 3 to 6 is introduced into an atomizer and struck by a stream of inert gas, generally air, having a temperature of up to 130° C. The aqueous collagen solution, generally obtained by diluting a 1.0 to 2.0% by weight/volume gel of type I native collagen with slightly acidic water, preferably has a final pH of from 4 to 5 and a content of collagen of from 0.3 to 0.5% by weight/volume; the collagen powder is then preferably collected in a closed container which is in a form such that the powder maintains a moisture content of less than 15%.

The powered product thus obtained has generally a particle size of less than 150 microns; it is then screened through a number of sieves, in a way well known in the art, to obtain the desired particle dimension and particle distribution according to the present invention. If necessary, selected volumes of particles having the required dimensions, obtained from the above mentioned screening process, are mixed to obtain a collagen powder according to the invention.

The size of the particles of the powered collagen of the present invention may be measured by the method of European Pharmacopoeia 7.0-01/2010:20931, that is a method according to standards ISO 13320-1 (1999) and ISO 9276-1 (1998).

In the following table are reported the technical characteristics of an equipment suitable for carrying out the mentioned method.

TABLE 1

Particle Size method - Malvern Hydro 2000 S Instrument.
Technical Characteristics

| | |
|---|---|
| Model | Malvern Mastersizer 2000 + Hydro S |
| Principle | Laser diffraction |
| Range | 0.02-2000 μm |
| Calculation model | Fraunhofer |
| Redox SOP | STR 071 (Ed.02) |
| | METSPEC 027 (Ed.01) |
| Frequency of QP check | Every 3 months |
| Dispersant | Tegiloxan 3 (R.I. 1.393) |
| Particle Refraction Index | 1.6 |
| Particle Absorption Index | 0.01 |
| Volume disperdant | About 150 mL* |
| Stirrer speed | 2800 RPM |
| Ultrasound Power | 100% |
| Standard for calibration | Glass beads QAS3001B |

| | $D_{10}$ (μm) | $D_{50}$ (μm) | $D_{90}$ (μm) |
|---|---|---|---|
| Standard Specifications | 35-42 | 58-62 | 85-95 |

| | |
|---|---|
| Sample Amount | About 50-100 mg. |
| | The powder is added after a laser |
| | aligning test and background |
| | recording.** |
| Time Background | 10 seconds |
| Time Analysis | 10 seconds |
| Ultrasound duration for Collagen analysis | 1-2 min |

*The dispersant volume is assessed by a level sensor, set onto the dispersant type and physical characteristics(viscosity and refraction index). The volume is about 150 mL.
**After laser alignment, the instrument performs a background and is ready to accept the sample powder; it is necessary to add powder up to reach a laser intensity between 10-20% (normally, about 50-100 mg).

Another object of the present invention is to provide wound healing compositions comprising the powdered collagen mentioned above. Said compositions may be in the form of a spray, tubes, bottles or sachets containing the material; further to the powder collagen, excipients, carriers and adjuvants, well known in the art, may be added.

Suitable excipients and carriers are materials having moisture absorbing properties, either mineral materials and vegetal materials. A suitable vegetal carrier is starch powder, preferably obtained from rice or maize; suitable mineral carrier materials are e.g. kaolin and zeolites. In an exemplary embodiment the granulometry of the starch substantially follows the particle size distribution of the collagen particles, namely the starch has at least 99.5% of the particles having a maximum size of 80 microns and at least 25% by volume, preferably 25% to 45% by volume of the particles having a size of more than 30 microns, wherein 35% to 50% by volume of the particles have a size in the range of 20 to 70 microns. The particle size distribution of a mineral carrier may be different, namely their dimension may be smaller than that of the collagen particles; in any case the particles dimensions of a mineral carrier will fall within the above mentioned range of the collagen powder: at least 99.5% of the particles have a maximum size of 80 microns and no more than 10% by volume of particles have a size of 10 microns or less.

When the wound healing composition is in the form of a spray, it is necessary to add a suitable propellant gas known in the art for this purpose and use, such as e.g. n-butane. Suitable adjuvants are Silver, in particular colloidal silver, Zinc and honey used for their known biocide properties; a suitable amount of colloidal silver in the collagen containing composition is 5-10 ppm.

The wound healing properties of the product of the present invention have been tested by measuring the characteristics of the wound during the cicatrizing process, for example the volume of exudates, the speed of reduction of the wound surface, etc. The results show an unexpected improvement of the wound healing properties of the product of the present invention compared to those of the products of the prior art.

The invention will now be further disclosed with reference to the following non-limiting examples.

EXAMPLES

Example 1

Preparation of Collagen Powder According to the Invention

An aqueous solution of type I collagen from horse tendons was prepared with a concentration of 1.2% by weight, having a pH of 4.5. The aqueous collagen solution was obtained by diluting a 1.8% by weight gel of type I native collagen with slightly acidic water, to said final pH of 4.5 and a content of collagen of 1.0% by weight.

The aqueous solution was introduced into an atomizer and struck by a stream of inert gas, having a temperature of up to 130° C. The obtained powder was sieved to have a granulometry distribution such that the particle size is in the range of 5 microns to 80 microns, inclusive, 40% by volume of the particles have a size of more than 30 microns, 20% by volume of the particles have a size of more than 40 microns and 12% by volume of the particles have a size of more than 50 microns.

The collagen powder of the present invention contains a maximum of 10% by volume of particles having a size of 10 microns or less.

Example 2

Preparation of a Spray Composition

The above prepared powder of example 1 was formulated as a composition that included rice starch. The granulometry of the rice starch substantially follows the particle size distribution of the collagen particles, namely the rice starch has at least 99.5% of the particles having a maximum size of 80 microns and at least 25% by volume, preferably 25% to 45% by volume of the particles having a size of more than 30 microns, wherein 35% to 50% by volume of the particles have a size in the range of 20 to 70 microns.

The composition of Example 2 was used for treating wounds and showed improved properties, namely a greater speed of reduction of the wound area and a reduction of the volume of exudates from the wound. At the same time the composition showed excellent flowability and an homogeneous distribution of the powder.

The composition of Example 2 was further used for treatment of diaper dermatitis in infants, showing to be at least as effective as zinc oxide, but with all the advantages of being administered as a spray.

The invention claimed is:

1. A collagen powder, wherein at least 99.5% of the particles have a maximum size of 80 microns and 25% to 45% by volume of the particles have a size of more than 30 microns.

2. A collagen powder according to claim 1, wherein 30 to 35% by volume of the particles have a size greater than 30 microns.

3. A collagen powder according to claim 1, wherein the amount of particles having a size greater than 40 microns is in the range of 15% to 22% by volume.

4. A collagen powder according to claim 3, wherein 20 to 22% by volume of the particles have a size greater than 40 microns.

5. A collagen powder according to claim 1, wherein the amount of particles having a size of more than 50 microns is in the range of 8 to 13% by volume.

6. A collagen powder according to claim 5, wherein the amount of particles having a size of more than 50 microns is in the range of 10 to 12% by volume.

7. A collagen powder according to claim 1, wherein the amount of particles having a size of 10 microns or less is 10% by volume or less.

8. A collagen powder according claim 1, wherein the amount of particles having a size within 10 to 20 microns is in the range of 25% to 35%, by volume.

9. A collagen powder according to claim 8, wherein the amount of particles having a size within 10 to 20 microns is in the range of 30% by volume.

10. A collagen powder according claim 1, wherein 35% to 50% by volume of the particles have a size in the range of 20 to 70 microns.

11. A collagen powder according to claim 1, wherein said collagen is a type I collagen obtained from horse and/or bovine tendons.

12. A pharmaceutical, medical or cosmetic composition comprising the collagen powder according to claim 1 and a carrier.

13. A composition according to claim 12, wherein said carrier is a solid and has a particle size distribution according to which at least 99.5% of the particles have a maximum size of 80 microns and the amount of particles having a size of 10 microns or less is 10% by volume or less.

14. A composition according to claim 13, that is a spray composition.

15. A composition according to claim 12, wherein said carrier is selected from the group consisting of rice starch, maize starch, kaolin, zeolites and mixtures thereof.

16. A composition according to claim 12, further comprising an adjuvant selected from the group consisting of silver, zinc, honey and mixtures thereof.

* * * * *